United States Patent [19]

Witty et al.

[11] Patent Number: 4,608,231

[45] Date of Patent: Aug. 26, 1986

[54] SELF-CONTAINED REAGENT PACKAGE DEVICE FOR AN ASSAY

[75] Inventors: Thomas R. Witty, Sandy, Utah; Robert E. Curry, Ramsey, N.J.; Roger E. Smith, Bountiful, Utah

[73] Assignee: Becton, Dickinson and Company, Franklin Lakes, N.J.

[21] Appl. No.: 740,593

[22] Filed: Jun. 3, 1985

Related U.S. Application Data

[63] Continuation-in-part of Ser. No. 681,034, Dec. 12, 1984.

[51] Int. Cl.⁴ .............................................. G01N 33/53
[52] U.S. Cl. .................................... 422/61; 422/58; 422/102; 422/104; 206/569; 435/808; 356/246
[58] Field of Search .................... 422/57, 58, 61, 101, 422/102, 104; 436/165, 807, 808; 435/300, 301, 311, 810; 206/569; 356/246

[56] References Cited

U.S. PATENT DOCUMENTS

| | | | |
|---|---|---|---|
| 3,585,285 | 6/1971 | Hamilton | 422/61 |
| 3,825,410 | 7/1974 | Bagshawe | 424/12 |
| 3,932,141 | 1/1976 | Beall et al. | 141/325 |
| 4,090,850 | 5/1978 | Chen et al. | 422/101 |
| 4,160,803 | 7/1979 | Potts | 422/101 |
| 4,251,159 | 2/1981 | White | 422/58 |
| 4,256,724 | 3/1981 | Rutner et al. | 424/1 |
| 4,272,478 | 6/1981 | Uihko | 422/58 |
| 4,383,041 | 5/1983 | Kutsusawa et al. | 435/291 |
| 4,387,164 | 6/1983 | Hevey et al. | 422/56 |
| 4,425,438 | 1/1984 | Bawman et al. | 422/57 |
| 4,534,939 | 8/1985 | Smith et al. | 422/61 |

FOREIGN PATENT DOCUMENTS

| | | | |
|---|---|---|---|
| 3690 | 10/1982 | Int'l Pat. Institute | 422/101 |
| 54440 | 4/1980 | Japan | 422/61 |

Primary Examiner—David L. Lacey
Attorney, Agent, or Firm—Richard J. Rodrick

[57] ABSTRACT

A self-contained reagent package device for an assay comprises a support member and a plurality of wells in the support member. All of the wells are capable of retaining liquids therein. One of the wells has on its interior surfaces an immunoreactive substance for carrying out the assay. At least one of the wells includes a predetermined amount of reagent therein. Another of the wells is empty so that the specimen to be assayed may be deposited therein. A protective cover is sealed over the open ends of the wells to maintain the incorporated reagents in stable form prior to use. The cover preferably does not seal the open end of one of the wells which serves as a specimen collecting well.

17 Claims, 4 Drawing Figures

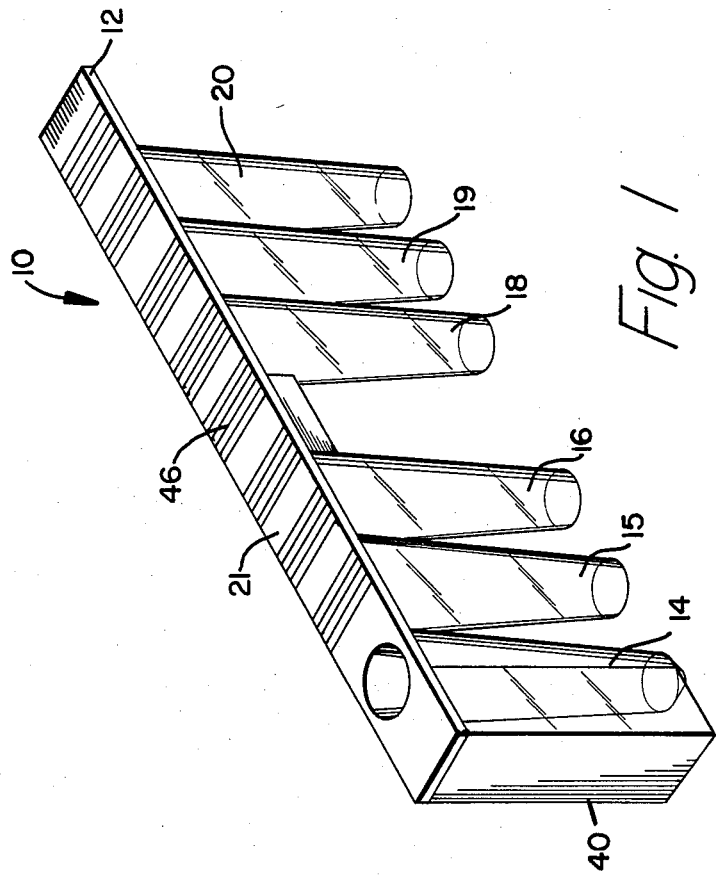

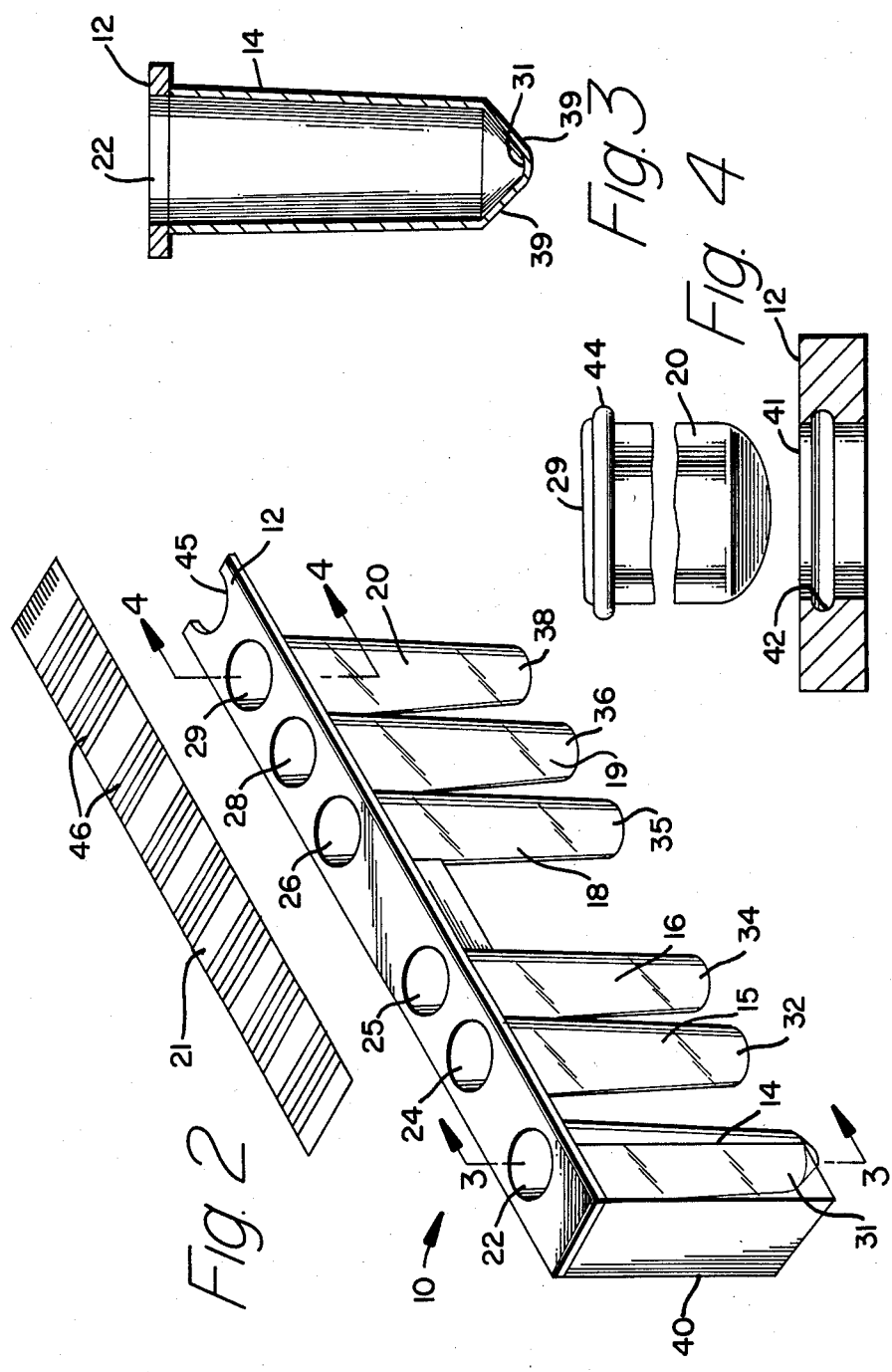

SELF-CONTAINED REAGENT PACKAGE DEVICE FOR AN ASSAY

This application is a continuation-in-part application of Ser. No. 681,034 filed on Dec. 12, 1984.

BACKGROUND OF THE INVENTION

1. Field of the Invention

The present invention relates to a device for performing an assay, and more particularly concerns a self-contained reagent package device useful in the performance of chemical and biological assays.

2. Description of the Prior Art

Test devices and procedures for assaying chemical and biological liquids are commonly known and used in laboratory practices. Assays are performed to determine trace amounts of many organic materials including drugs, contaminants, pollutants and the like. Similarly, assays are performed on biological liquids such as serum, urine, cerebrospinal fluid and peritoneal exudates. Different types of assays have been employed depending upon the analyte of interest, and include radioimmunoassays (RIA), enzyme-linked immunosorbent assays (ELISA), immunoradiometric assay (IRMA), immunofluorometric assay (IFMA), and other various immunoassays.

Even though assays have been carried out for many years and there are devices which seek to simplify and accurately perform the assays, the need continues for further improvements in assay devices. For example, cross-contamination still remains troublesome, as well as delays for reagent changeover during the assay procedures. Frequent transfer or the pipetting of materials is still involved which could cause inaccuracies of the results. Further, the preparation and pattern of using reagents causes drawbacks in the methodology of the assay procedures, particularly if specific agents are required in non-specialized laboratories.

Various assay devices and procedures have been taught in the prior art. For example, U.S. Pat. No. 3,825,410 describes a disposable combined storage and reaction cell for use in the performance of chemical and biological reactions. This reaction cell is designed to facilitate dispensing the reactants into a container of suitable size and form and the stabilization of the reactants so dispensed. Improvements in storage and transportation under various conditions of temperature and humidity are also described. The patented invention further provides for the addition of sample diluent or other agents and the initiation of the reaction, and finally the separation of the component to be measured from the other components of the reaction.

In U.S. Pat. No. 4,090,850, an apparatus is described for use in radioimmunoassays. Such apparatus includes a receptacle tray with a multiplicity of wells. Each of the wells has at its bottom an orifice sized and shaped to retain the liquids used in the assay under given pressure conditions. The orifice, however, permits the evacuation of liquids therethrough at reduced pressure. This patented invention is said to simplify the manipulative steps that the laboratory technician must use, as well as obviate the need for aspiration of the liquids to be tested.

A test apparatus for the determination of immunoassays of antigens and antibodies is described in U.S. Pat. No. 3,932,141. In that invention, the apparatus includes a receptacle tray with a plurality of wells for receiving samples, and balls coated with an immunologic composition. Use of these coated balls is said to effectuate improvements in reproducibility and exactness in radioimmunoassay techniques.

In U.S. Pat. No. 4,160,803, a self-packaged test kit is described. The self-packaged structure is used as a kit for handling and carrying out tests utilizing collection tubes and fraction columns, including a plurality of modular laboratory racks.

An automatic enzyme immunoassay apparatus is described in U.S. Pat. No. 4,383,041. That apparatus includes a rack for holding test tubes; in the test tubes are beads which provide surfaces for the immunochemical reactions.

Notwithstanding the devices and procedures described in the aforementioned prior art, as well as other known and used assay devices, there is room for further improvement in this area. It is to such improvements that the present invention is directed.

SUMMARY OF THE INVENTION

The self-contained reagent package device of the present invention is useful for an assay and includes a support member and a plurality of wells in the support member. All of the wells are capable of retaining liquids therein. One of the wells has on its interior surfaces an immunoreactive substance for carrying out the assay. At least one of the wells includes a predetermined amount of reagent therein. Another of the wells is empty so that the specimen to be assayed may be deposited therein. A protective cover is sealed over the wells to maintain the incorporated reagents in stable form prior to use.

In a preferred embodiment of the present invention, the support member is a plate or a flat strip. A plurality of wells is integrally formed as a unitary structure with and from the same material as the support member. A removable well is also included in the support member. All of the wells are preferably arranged in single file in the support member and have open top ends for access thereto. The open top ends of the wells lie in substantially the same plane coextensive with the support member. It is preferred that the removable well be positioned at one end of the support member and be made from substantially optically clear material.

In accordance with the principles of the present invention, a self-contained reagent package device is provided. While many advantages and features result from the present invention, which will become apparent from a reading of the description which follows, there are some notable distinctions that should be mentioned. For example, all reagents for the assay procedure of interest, including the immunoreactive substance inside the removable well, are specific to that assay and are self-contained in the package. This ameliorates problems involved in assay to assay changeover, and means that an assay may be performed with no delay for reagent changeover. The configuration of the present invention is versatile thereby allowing a wide selection of wells, assay materials and reagents which may all be selected so as to be assay specific. Moreover, the present reagent package is readily adaptable for use in many different assays, such as fluoroimmunoassays, immunofluorometric assays, nephelometric assays and the like. The optically clear well may be positioned in the path of an excitation light beam so that fluorescent markers or light scatter may be detected during the assay procedures. Laboratory use of the present device is simplified and straightforward.

BRIEF DESCRIPTION OF THE DRAWINGS

FIG. 1 is a perspective view of the preferred self-contained reagent package device of the present invention;

FIG. 2 is a perspective view of the device of FIG. 1 with the protective cover removed;

FIG. 3 is a cross-sectional view of the specimen well taken along line 3—3 of FIG. 2; and FIG. 4 is an enlarged cross-sectional view taken along line 4—4 of FIG. 2 illustrating the snap-fit features of the removable well and the support member.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting now to the drawings, and FIGS. 1 and 2 in particular, there is illustrated the preferred self-contained reagent package device 10. Comprising this device are three major components: a support member 12, a plurality of wells herein designated by the numerals 14,15,16,18,19 and 20, and a protective cover 21, which in the embodiment being described is removable. In other embodiments contemplated by the present invention, protective cover 21 is pierceable in order to gain access to the wells.

Support member 12, in the embodiment being described, is preferably a flat plate or substantially planar strip of material having sufficient rigidity to maintain the wells in fixed position for the performance of the various tests. In this embodiment, the wells are linearly arranged in single file in the support member so that the top ends of the wells are joined to the support member while the bottom ends of the wells depend freely downwardly. This free arrangement of the bottom ends of the wells allows the wells to be positioned in a suitable stand during use and also allows clear visual observation of the contents of the wells, particularly if they are made out of transparent or translucent material. It can be seen that all of the wells have open top ends for access into the wells, these openings designated by numerals 22,24,25,26,28 and 29, corresponding respectively with each of the wells. All of the open top ends of the wells preferably lie substantially in the same plane and, as illustrated, are substantially coextensive with the planar support member.

For purposes of the present invention, it is preferred that all of the wells have closed bottom ends, designated by numerals 31,32,34,35, 36 and 38, corresponding respectively to each of the above-described wells. In the most preferred configuration, the closed bottom ends of the wells are smoothly curved, rounded ends, except for the closed end of well 14.

Well 14 is expected to be the specimen-carrying well. In order to be able to withdraw or transfer precise or small amounts of liquid from well 14, it is preferred that its bottom end 31 be conically-shaped with inwardly tapering surfaces 39, as illustrated in FIG. 3.

The reagent package device of the present invention is expected to be utilized in a chemical analyzer which may include a number of automated operations. Along these lines, it is expected that well 20 will include the substances relating to the immune reaction or absence thereof and will be used as the vehicle for performing the test, particularly for a fluoroimmunoassay or an immunofluorometric assay. To this end a wall 40 extends downwardly from support member 12 and may be anchored at its bottom end to the bottom of well 14. Wall 40 serves as a keying feature to make sure the present reagent package device is inserted properly, and with well 20 facing the right direction, in an analyzer instrument so that the contents of well 20 may be properly analyzed.

Referring now to well 20, in its preferred embodiment it is made from a material different from the other wells. Accordingly, while the other wells are preferably integrally formed with support member 12, well 20, being separately formed, is added to the package as a subsequent assembly. Support member 12 includes a hole 41 therethrough and a detent 42 slightly recessed below the upper surface of the support member. Near open end 29 of well 20 an annular lip 44 is included. Lip 44 is intended to cooperate with detent 42 in the support member so that well 20 may be snap-fit into the support member. This type of fit allows stability of the well when positioned in the support member, while permitting its easy insertion into the support member. Well 20 may even be removed from the support member, if desired.

Before well 20 is inserted into the support member, it may be treated with an immunoreactive substance for carrying out the particular assay which is desired. For example, in the preferred embodiment of the present invention, all of the wells, including well 20, are plastic tubes. The interior surfaces, including the inside walls and the bottom, of well 20 serve as a solid substrate onto which the immunoreactive substance is coated. If the immunoassay is a test for antibody, the immunoreactive substance to be coated on the interior surfaces of well 20 is an antigen or hapten, or any appropriate analogue thereof. On the other hand, if the immunoassay test is for the antigen or hapten, then the interior surfaces of well 20 are coated with antibody.

If antibody is to be coated onto the interior walls of well 20, the coating is carried out by general procedures known in the art. Typically, the coating is effected at room temperatures, although higher or lower temperatures may be employed. Also, the antibody titer of the dilute antibody solution should be at a value to provide the desired antibody coating. One technique for coating antobodies to a solid substrate such as the walls of a test tube is described in U.S. Pat. No. 4,256,724.

With respect to the other wells, they may either be empty or contain other liquids or reagents. Well 14 at one end of the support member, for example, is preferably left empty so that the specimen to be assayed may be deposited therein. Depending upon the specific assay to be performed, and merely for exemplary purposes, well 19 may contain an elution buffer or a substrate; well 18 may be used for mixing the diluent and the specimen, if required; well 16 may contain a diluent, if required; and well 15 may contain a tracer if necessary for the particular assay. Of course, different materials, reagents, liquids and the like, as well as different numbers of wells, may be selected for the particular assay to be performed.

To provide a self-contained reagent package, cover 21 is provided. This cover is preferably sealed to the planar surface of support member 12 so as to effectively close open top ends 24,25,26,28 and 29 of the wells corresponding respectively thereto. It is preferred that cover 21 leave top end 22 of the well 14 uncovered since that well is preferably empty and is in ready condition to accept the specimen to be assayed. Cover 21 may be affixed to support member 12 by any convenient mechanism for assuring a tight seal while, in one embodiment, allowing the cover to be removed when the device is ready for use. A finger, notch 45 may be included in one end of support member 12 so as to facilitate the gripping of the end of cover 21 for removal purposes. In another embodiment, rather than removal, the cover may be pierced or punctured by a probe or other sharp instrument to gain access to the interior of the various wells.

It can be seen in the drawings that protective cover 21 includes labeling information 46 on its upper surface. This labeling information may indentify the various reagents contained within the wells, the type of assay to be performed, dates of manufacture and use, and other information that may be useful for information control purposes. In the embodiment being described, it is preferred that the labeling information be in the form of a bar code adapted to be read electronically to determine the information imprinted thereon. These bar codes are well-known and the information with respect to different bar configurations may be pre-programmed into a microprocessor so that once a recognizable code has been electronically read, that information may be retrieved, displayed, stored or otherwise acknowledged. Of course, human readable information may be included on the cover for labeling purposes.

As a self-contained reagent package device, the present invention maintains the incorporated reagents in stable form prior to use. A typical assay procedure in which device 10 is used will now be described. This typical assay procedure is merely exemplary as it may relate to the one configuration of the reagent package device illustrated in the drawings. No limitations with respect to the scope of the present invention should be attributed to the following description.

If, for example, blood serum is to be assayed for a determination of trace amounts of proteins, hormones, drugs or the like, the prepared serum is deposited in well 14. Either before the specimen is placed in well 14 or immediately thereafter, protective cover 21 may be removed from rack 12 or pierced by a sharp instrument so as to expose the open top ends of the remaining wells of the pre-packaged device. A measured amount of the serum is withdrawn from well 14. In serial fashion, diluent is withdrawn from well 16, and both are transferred to well 18. Once diluted and mixed in well 18, a measured amount of the diluted specimen is withdrawn. In serial fashion a tracer material is withdrawn from well 15, and both are transferred to well 19. There, the tracer reacts with one or more components of the diluted serum. Radioactive, fluorescent and the like materials are typically used as tracers.

After sufficient time has passed to allow the tracer to react with the components of diluted serum, a measured amount of the reacted mixture in well 19 may be withdrawn and deposited in well 20. As described above, well 20 may, for example, have its interior surfaces coated with antibody. The mixture with tracer having appropriate antigenic reactants causes an immune reaction within well 20 whereby select substances bind to the antibodies on the surfaces of the well. A wash usually follows so as to remove unbound substances as well as soluble substances from well 20.

If, for example, a fluoroimmunoassay is being performed, fluorescent labels may be detected directly in well 20 after the immune reaction has taken place. Well 20 may either be removed from the reagent package device or left within the device, depending upon the instrumentation being used to carry out the fluoroimmunoassay. Well 20, as mentioned above, is preferably fabricated from a substantially optically clear material, such as glass or clear plastic, so as to facilitate the passage of light into the interior of the well. The liquid solution of fluorescent molecules within well 20 is excited with light of constant intensity and at an appropriate wavelength. Fluorescence emission is detected and serves as a function of the quantity of the antigenic substance which was present in the sample.

While many different materials may be used to construct the present reagent package device, plastic is the material of choice. Preferably, a rigid, transparent or translucent plastic, such as polypropylene is selected for the present invention. Use of plastic material also allows the support member and wells to be formed in a molding operation. In particular, the wells, except for well 20, are preferably integrally formed as a unitary structure with and from the same material as the support member. This not only facilitates the manufacturing operation, but allows the device to be inexpensively made so as to render it disposable after use. Such a unitary structure is desirably fabricated from polypropylene. On the other hand, well 20 may be molded separately and also from a different material. Inasmuch as the optical and chemical properities of polystyrene are better than polypropylene for some assay types, it is the material of choice for well 20 particularly when the present reagent package device is to be employed for fluoroimmunoassays. In other circumstances, it may be desirable to make well 20 out of glass.

Thus, the present invention provides a self-contained reagent package device wherein all of the reagents necessary for the assay are pre-prepared for ease of use by the laboratory technician. The present reagent package device may be inexpensively fabricated and is disposible after one use. Moreover, the present invention may be utilized in conjunction with automated chemistry or immunochemistry analyzers, and is particularly suitable for a variety of assays, including fluoroimmunoassays.

What is claimed is:

1. A self-contained reagent package device useful in the performance of chemical and biological assays comprising:
    a substantially planar support member;
    a plurality of wells in said support member, all of said wells having open top ends for access thereto, and all but one of said wells being integrally formed as a unitary structure with and from the same material as said support member, said one well having its interior surfaces coated with an immunoreactive substance for carrying out the assay;
    at least one of said integrally formed wells having a predetermined amount of reagent therein;
    another of said integrally formed wells being empty so that the specimen to be assayed may be deposited therein; and
    a protective cover sealed over the open ends of said wells to maintain the incorporated reagents in stable form prior to use thereby providing a self-contained reagent package device.

2. The device of claim 1 wherein the open top ends of said wells lie substantially in the same plane.

3. The device of claim 2 wherein said support member is a substantially planar strip having the open top ends of said wells coextensive therewith.

4. The device of claim 3 wherein said wells are linearly arranged in single file in said support member.

5. The device of claim 4 wherein said coated well is positioned at one end of said support member and said empty well for the specimen is positioned at the other end of the support member.

6. The device of claim 1 wherein the protective cover is positioned on the open top ends of the wells such that the empty specimen well is uncovered.

7. The device of claim 1 wherein said support member and all of said wells are made of plastic.

8. The device of claim 7 wherein said coated well is made from a plastic different from the plastic of said integrally formed wells.

9. The device of claim 8 wherein said coated well is made from polystyrene and said integrally formed wells and said support member are made from polypropylene.

10. The device of claim 1 wherein said coated well is made from a material which is substantially optically clear.

11. The device of claim 1 wherein said protective cover includes labeling information thereon relating to the nature of the assay to be performed.

12. The device of claim 11 wherein said information is in the form of a bar code constructed and arranged so as to be read electronically to determine said information.

13. The device of claim 1 wherein the immunoreactive substance on the interior surface of the coated well is antibody.

14. The device of claim 1 wherein the empty well for the specimen has a conically-shaped bottom end.

15. The device of claim 1 which further includes keying means for assuring that the device is insertable into analyzer means in a predetermined direction.

16. The device of claim 1 wherein said coated well has a lip around its open end and said support member has a detent formed therein so that said coated well is snap-fit in said support member.

17. A self-contained reagent package device useful in the performance of chemical and biological assays comprising:

a substantially planar strip member;

a plurality of wells in said strip member, all but one of said wells being integrally formed as a unitary structure with and from the same material as said member;

all of said wells being arranged in single file in said member and having open top ends for access thereto with said open top ends lying in substantially the same plane coextensive with the member, the non-integrally formed well being positioned at one end of said member and made from substantially optically clear material and having its interior surfaces coated with an immunoreactive substance for carrying out the assay;

at least one of said integrally formed wells having a predetermined amount of reagent therein;

one of said integrally formed wells at the other end of the member being empty so that the specimen to be assayed may be deposited therein, said specimen well having a conically-shaped bottom end; and a protective cover sealed over the open ends of said wells except said empty specimen well to maintain the incorporated reagents in stable form prior to use, said cover including labeling information thereon in the form of a bar code constructed and arranged so as to be read electronically to determine said information.

* * * * *